United States Patent [19]

Barney et al.

[11] Patent Number: 5,370,863
[45] Date of Patent: Dec. 6, 1994

[54] ORAL CARE COMPOSITIONS CONTAINING HOP ACIDS AND METHOD

[75] Inventors: Michael C. Barney, Elm Grove; Edward J. Kot, Delafield; Etzer Chicoye, Milwaukee; Janna K. Jilek, West Allis, all of Wis.

[73] Assignee: Miller Brewing Company, Milwaukee, Wis.

[21] Appl. No.: 991,613

[22] Filed: Dec. 16, 1992

[51] Int. Cl.$^5$ .............................................. A61K 7/26
[52] U.S. Cl. ...................................... 424/49; 424/76.1; 424/76.8; 424/76.9; 426/600
[58] Field of Search ............ 424/49, 76.1, 76.8, 424/76.9; 426/600

[56] References Cited

U.S. PATENT DOCUMENTS

| 3,751,266 | 8/1973 | Kuroiwa et al. | 426/600 |
| 3,932,603 | 1/1976 | Haas | 424/49 |
| 4,148,873 | 4/1979 | Owades | 424/59 |
| 4,170,638 | 10/1979 | Owades | 424/65 |
| 4,644,084 | 2/1987 | Cowles et al. | 568/341 |
| 4,647,464 | 3/1987 | Todd, Jr. et al. | 426/423 |
| 4,786,492 | 11/1988 | Ratcliff | 424/53 |
| 4,851,213 | 7/1989 | Ratcliff | 424/53 |
| 4,877,603 | 10/1989 | Degenhardt et al. | 424/57 |
| 4,906,573 | 3/1990 | Barney et al. | 435/243 |
| 5,066,483 | 11/1991 | Harkrader et al. | 424/54 |
| 5,082,975 | 1/1992 | Todd, Jr. et al. | 568/315 |
| 5,200,227 | 4/1993 | Guzinski et al. | 426/600 |

FOREIGN PATENT DOCUMENTS 1112182 11/1981 Canada.

Primary Examiner—Thurman K. Page
Assistant Examiner—Robert H. Harrison
Attorney, Agent, or Firm—Quarles & Brady

[57] ABSTRACT

Oral care compositions containing hop acids or their salts are effective in inhibiting Gram positive bacteria which can cause plaque or periodontal disease. A representative composition is a toothpaste containing tetrahydroisohumulone.

2 Claims, No Drawings

ORAL CARE COMPOSITIONS CONTAINING HOP ACIDS AND METHOD

FIELD OF THE INVENTION

This invention relates to oral care compositions which contain hop acids and to a method for inhibiting undesirable Gram positive microorganisms in the oral cavity.

BACKGROUND OF THE INVENTION

It is generally believed that bacterial plaque is directly associated with dental caries and periodontal disease. Plaque is formed by a combination of events starting with a salivary coating which forms on the teeth to which various forms of Streptococcus adhere. The Gram positive Streptococcus, principally *S. mutans* and *S. sanguis*, with the assistance of bacterially produced enzymes form dextrans from sucrose which is in the oral cavity. The dextrans serve as nutrients which support the growth of additional organisms which produce acids which can demineralize both enamel and dentin and cause dental caries and decay. In addition to dental caries, gingivitis and other periodontal diseases are known to be caused by bacteria.

It was known in the brewing industry that some hop acids can inhibit the growth of the microorganisms that can cause spoilage in beer. For example, the Todd Jr. et al. U.S. Pat. No. 5,082,975 discloses that the hop acid, hexahydrocolupulone, can inhibit the growth of certain Lactobacillus. However, no literature or patents of which we are aware disclose or suggest that hop acids might be useful to inhibit the microorganisms that cause dental caries and periodontal disease.

BRIEF SUMMARY OF THE INVENTION

It is an object of the present invention to disclose novel oral care compositions which inhibit the microorganisms that cause plaque and periodontal disease.

It is also an object to disclose a method of inhibiting plaque and periodontal disease employing the novel compositions of the present invention.

The novel oral care compositions of the present invention are those which contain the hop acids, tetrahydroisohumulone, tetrahydroisoadhumulone, tetrahydroisocohumulone, Rho-isohumulone, Rho-isoadhumulone, Rho-isocohumulone, lupulone, adlupulone, colupulone, hexahydrolupulone, hexahydroadlupulone, hexahydrocolupulone, mixtures thereof, and the salts thereof, in combination with suitable pharmaceutically acceptable carriers.

The novel oral care compositions of the present invention are toothpastes, tooth powders, mouthwashes, gums and the like which are formulated for administration to the oral cavity. Normally, such compositions will contain about 1.0 to 100 parts per million (ppm) or about 0.0001–0.0100% weight percent of one or more hop acids or their salts.

The novel method of inhibiting undesirable gram positive microorganisms in the oral cavity basically comprises introducing a novel oral care composition of the present invention into the oral cavity so that the hop acid(s) can inhibit the Gram positive microorganisms that may be present. The spent composition is then preferably removed, however, it can be ingested without any detrimental effects because of the proven safety of the hop acids.

It will be apparent to those skilled in the art that the above described and additional objects and advantages may be obtained by the practice of the present invention.

DETAILED OF THE PREFERRED EMBODIMENTS

The preferred oral care compositions are those which contain a safe and effective amount of a hop acid or a mixture thereof and/or the salts thereof in combination with a pharmaceutically acceptable carrier suitable for use in the oral cavity.

The preferred compositions of the present invention are formulated for use in the oral cavity without being ingested, except for ingestion that might incidentally occur during usage. In the preferred method of use, the composition will be administered to the oral cavity, kept there during treatment and subsequently removed when treatment is finished.

The phrases "oral administration" and "administered to the oral cavity," as used herein are meant to describe any method by which the compositions of the present invention are administered into the mouth and contacted with the teeth and gums. Such methods basically comprise bringing the compositions into contact with the teeth and gums, as well as with any calculus or plaque that may be present or form in the oral cavity. The contact may occur by rinsing, brushing with a toothbrush, bringing a solution containing the composition into contact with the teeth and/or gums.

The "oral compositions" of the present invention include powders, pastes, gels, solutions, and the like, for rinsing, brushing, washing or topical application in the oral cavity. These compositions include compositions for cleaning teeth, prophylactic compositions, such as antigingivitis compositions, and mouth rinses and other oral care compositions. The compositions may contain as active ingredients only the hop acids or may contain the hop acids in combination with other dentifrice, prophylactic, and oral care ingredients.

The phrase "pharmaceutically acceptable carrier" is intended to mean one or more hop acid-compatible solid or liquid diluents or encapsulating substances which are suitable for oral administration, such as application to or rinsing of the oral cavity e.g., mouth.

The concentration of the hop acid(s) in the oral care compositions should be at least an effective amount for providing the desired utility (i.e., calculus-inhibiting utility or plaque-inhibiting utility). While the total concentration of the hop acids in the oral composition can be between about 1.0 to 100 ppm or 0.0001 to 0.100 %, by weight, generally an oral care composition will contain between about 10 and 50 ppm, of the hop acid(s) or salts.

By "safe and effective amount" as used herein is meant an amount of a hop acid or salt thereof which is enough to provide anticalculus and/or antiplaque efficacy, preferably both, but not so high as to fall outside the scope of sound medical judgement. The safe and effective amount can vary with the particular hop acid chosen, the intended use of the composition, the duration of treatment, and the particular carrier with which the hop acid is combined. Generally the amount of the hop acid administered on a regular basis, in the form of the described oral compositions is an amount which is effective to inhibit the microorganisms without being too bitter.

The oral care compositions of the present invention preferably have a pH of between about 5.0 and about 9.0. A preferred pH range is about 7.0 to about 9.0. The compositions will be buffered, for example, by including a buffer in the carrier so that a pH of between about 5.0 and about 9.0 is maintained in the oral cavity during use. Exemplary nonlimiting buffers include citrate, citrate/bicarbonate, and phosphate buffers.

The carrier also can contain the usual components of the particular type of oral compositions desired. Such additional components can include abrasives, sudsing agents, flavoring agents, sweetening agents, coloring agents, pigments, humectants, binders (thickening agents), other anticaries agents, etc. The choice of carrier to be used is basically determined by the way the composition is to be introduced to the oral cavity and by the purposes for which the composition is meant to be effective. For example, if a toothpaste is to be used, then a "toothpaste carrier" is chosen containing abrasive materials, sudsing agents, binders, humectants, flavoring and sweetening agents, etc. If a mouth rinse is to be used, then a "mouth rinse carrier" containing water, flavoring and sweetening agents, possibly an organic solvent such as ethanol, etc. is chosen. Similarly, if a chewing gum is to be used, then a conventional "chewing gum carrier" containing gum base, flavoring and sweetening agents is chosen. Other carriers suitable for the preparation of the oral care compositions of the present invention are well known in the art.

Other active ingredients also can optionally be added to the compositions of this invention. Suitable antiplaque agents may include bis-biguanide compounds such as chlorhexidine (1,6-bis [N$^5$-p-chlorophenyl-N'-biguanido]hexane), the soluble and insoluble salts thereof, and related materials such as 1,2-bis(N$^5$-p-trifluoromethylphenyl-N'-biguanido)ethane. The composition of the present invention also can contain other anticalculus agents, or antitartar agents, such as the dialkali metal and mixtures of dialkali metal and tetraalkali metal pyrophosphate salts. If present, the optional antiplaque agents generally comprise from about 0% to about 5% by weight of the compositions herein.

The topical solutions and mouth rinses herein also may contain ethanol in an amount preferably of from about 0% to about 30%.

Water can also be present in the compositions of this invention. Water employed in the preparation of commercially suitable dentifrices, prophylactic compositions, and other oral care compositions should preferably be deionized and free of organic impurities. Water generally comprises from about 10% to 50%, preferably from about 20% to 40%, by weight of the toothpaste compositions herein. Mouth rinses generally contain from about 45% to about 95% water. These amounts of water include the free water which is added plus that which is introduced with other materials such as with sorbitol.

It is common to have a water-soluble fluoride compound present in dentifrices in an amount sufficient to give a fluoride concentration of from about 0.0025% to about 5.0% by weight, preferably from about 0,005% to about 2.0% by weight, to provide additional anticaries efficacy. Preferred fluorides are sodium fluoride, stannous fluoride, indium fluoride, and sodium monofluorophosphate.

The preferred hop acids ingredient of the oral compositions of the present invention is a mixture of tetrahydroisohumulone, tetrahydroisoadhumulone and tetrahydroisocohumulone. Other hop acid ingredients that can be used include Rho-isohumulone, Rho-isoadhumulone, Rho-isocohumulone, isohumulone, isoadhumulone, isocohumulone, lupulone, adlupulone, colupulone, hexahydrolupulone, hexahydroadlupulone, hexahydrocolupulone, the salts thereof and mixtures thereof.

The results of tests demonstrating the antimicrobial action of various mixtures of hop acids on microorganisms, including *S. mutans* and *S. sanguis*, are shown in Table 1.

TABLE 1

SUMMARY OF THE MINIMAL INHIBITORY CONCENTRATIONS (PPM) OF HOP COMPOUNDS ON VARIOUS MICROORGANISMS

| Test Organism | Hop Acid Mixture | | | |
| --- | --- | --- | --- | --- |
| | Tetrahydro-isohumulones | Rho-isohumulones | Hexahydro-colupulones | Colupulones |
| Gram Positive Bacteria | | | | |
| Pediococcus RB1 | >8<16$^a$ | >125<250 | none$^b$ | none |
| Pediococcus RB2 | >16<32 | >63<125 | none | —$^c$ |
| Pediococcus EP-404A | >4<8 | >32<63 | none | — |
| Lactobacillus delbrueckii PEL | >63<125 | >63<125 | none | none |
| Lactobacillus plantarum KGF50 | >32<63 | >125<250 | none | none |
| Lactobacillus plantarum KGF54 | >32<63 | >63<125 | none | none |
| Micrococcus PRT | >16<32 | >16<32 | >3.2<6.3 | >12.5<25 |
| Staphlococcus aureus | >16<32 | >16<32 | none$^b$ | >6.3<12.5 |
| Streptococcus pyogenes | >1<2 | >16<32 | none | none |
| Streptococcus pneumoniae | >4<8 | >8<16 | >0.2<0.4 | >25<50 |
| Streptococcus faecalis | >32<63 | >63<125 | none | none |
| Streptococcus mutans | >4<8 | —$^c$ | >12.5<25 | >8<16 |
| S. sanguis | >13<25 | —$^c$ | — | >25<50 |
| Bacillus cereus | >16<32 | >4<8 | >1.6<3.2 | >0.8<1.6 |
| Bacillus subtilus | >8<16 | >8<16 | >0.8<1.6 | >3.2<6.3 |
| Listeria monocytogenes ScottA | >8<16 | >8<16 | >0.4<0.8 | >12.5<25 |
| Listeria innocua | — | — | >0.8<1.6 | — |

TABLE 1-continued

SUMMARY OF THE MINIMAL INHIBITORY CONCENTRATIONS (PPM) OF HOP COMPOUNDS ON VARIOUS MICROORGANISMS

| | Hop Acid Mixture | | | |
|---|---|---|---|---|
| Test Organism | Tetrahydro-isohumulones | Rho-isohumulones | Hexahydro-colupulones | Colupulones |
| *Listeria seeligeri* | — | — | >0.4<0.8 | — |
| *Propionibacterium acnes* | >8<16 | >8<16 | >4<8 | >32<64 |

[a] "greater than 8 but less than 16 inhibited
[b] "none" = none of the concentrations tested were found to be inhibitory
[c] "—" = not tested Gram Negative Bacteria

| | | | | |
|---|---|---|---|---|
| *Escherichia coli* | none[a] | none | none | none |
| *Salmonella typhimurium* | none | none | —[b] | — |
| *Pseudomonas aeruginosa* | none | none | — | — |
| Yeasts *Candidia albicans* | none | none | none | none |

[a] "none" = none of the concentrations tested were found to be inhibitory
[b] "—" = not tested The practice of the present invention is further illustrated by the examples which follow:

EXAMPLE 1

The following is a representative example of a toothpaste that could be made employing the teachings of the present invention.

| Ingredient | % w/w |
|---|---|
| Sorbitol (70% Aqueous Solution) | 49.56 |
| Sodium Saccharin | 0.30 |
| Dye Solution | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940 | 0.20 |
| Xanthan Gum | 0.60 |
| Tetrahydroisohumulone (25 ppm) | 0.0025 |
| Distilled Water q.s. ad. | 100.00 |

The above composition would be made by combining the water and part of the sorbitol in an agitated mixture and heating this mixture to 140° F. The tetrahydroisohumulone [in ethanol solution], saccharin, sodium fluoride and precipitated silica would then be added in order and the total mixture mixed for from 5 to 10 minutes. The flavor, dye and surfactant would then be added. In a separate vessel the remainder of the sorbitol, the Carbopol and the xanthan gum would be slurried together and then added to the main mix tank. The complete batch would then be mixed for about one-half hour and subsequently milled and deaerated.

EXAMPLE 2

The following is another representative toothpaste which could be made employing the teachings of the present invention.

| Ingredient | % w/w |
|---|---|
| Sorbitol (70% Aqueous Solution) | 50.75 |
| Sodium Saccharin | 0.30 |
| Dye Solutions | 0.35 |
| Precipitated Silica | 20.00 |
| Sodium Fluoride | 0.25 |
| Flavor | 1.30 |
| Sodium Alkyl Sulfate (27.9% Aqueous Solution) | 5.00 |
| Carbopol 940 | 0.20 |
| Xanthan Gum | 0.60 |
| Rho-isohumulone | 0.0050 |

-continued

| Ingredient | % w/w |
|---|---|
| Distilled Water q.s. ad. | 100.00 |

The toothpaste could be prepared as described in Example I.

In addition to the levels and combinations of ingredients shown in these examples, others might be used which are consistent with the invention disclosed.

EXAMPLE 3

The following is an example of a mouth rinse composition which could be made employing the teachings of the present invention.

| Ingredient | % |
|---|---|
| Tetrahydroisohumulone | 0.0025 |
| Ethanol | 16.25 |
| Glycerin | 10.00 |
| Nonionic Surfactant | 0.12 |
| Benzoic Acid | 0.05 |
| Sodium Saccharin | 0.05 |
| Flavor | 0.15 |
| Color | 0.04 |
| Sodium Hydroxide (10% sol.) | 0.15 |
| Distilled Water q.s. ad. | 100.00 |

The mouth rinse would be prepared by adding each of the ingredients to the distilled water with stirring until a solution is obtained.

The salts of the hop acids which can be used to prepare the oral care compositions of the present invention are preferably the sodium and potassium salts. They are easily prepared and quite soluble. The salts may be preferred when it is desired to make an oral care composition without adding alkali buffering agents.

It will be readily apparent to those skilled in the art that an umber of modifications and changes can be made without departing from the spirit and scope of the invention. Therefore, it is intended that the invention be limited only by the claims.

We claim:

1. An oral care composition selected from a toothpaste and tooth power, said composition comprising about 0.0001 to 0.0100% by total weight of a compound which inhibits *Streptococcus mutans*, said compound being selected from the group consisting of tetrahydroisohumulone, tetrahydroisadhumulone, tetrahydroisocohumulone and mixtures thereof.

2. An oral care composition of claim 1 in which the composition is a toothpaste containing tetrahydroisohumulone.

* * * * *